United States Patent
Kjellman et al.

(10) Patent No.: US 6,886,411 B2
(45) Date of Patent: May 3, 2005

(54) PIEZOELECTRIC SENSOR IN A LIVING ORGANISM FOR FLUID PRESSURE MEASUREMENT

(75) Inventors: Charlotte Kjellman, Stockholm (SE); Johan Lidman, Stockholm (SE); Karin Ljungström, Hasselby (SE); Kenth Nilsson, Åkersberga (SE)

(73) Assignee: St. Jude Medical AB, Järfälla (SE)

( * ) Notice: Subject to any disclaimer, the term of this patent is extended or adjusted under 35 U.S.C. 154(b) by 0 days.

(21) Appl. No.: 10/399,813

(22) PCT Filed: Oct. 24, 2001

(86) PCT No.: PCT/SE01/02345
§ 371 (c)(1),
(2), (4) Date: Sep. 24, 2003

(87) PCT Pub. No.: WO02/34130
PCT Pub. Date: May 2, 2002

(65) Prior Publication Data
US 2004/0060362 A1 Apr. 1, 2004

(30) Foreign Application Priority Data
Oct. 24, 2000 (SE) .............................. 0003852

(51) Int. Cl.⁷ ................................. G01L 7/00
(52) U.S. Cl. ........................................ 73/756
(58) Field of Search .................. 73/706, 720, 721, 73/726, 727, 754, 756; 600/437, 438, 458, 485, 486, 549

(56) References Cited

U.S. PATENT DOCUMENTS

| 4,432,372 | A | * | 2/1984 | Monroe | 600/488 |
| 4,471,786 | A | * | 9/1984 | Inagaki et al. | 600/561 |
| 4,600,017 | A | | 7/1986 | Schroeppel | |
| 5,150,616 | A | * | 9/1992 | Kondo et al. | 73/514.33 |
| 5,271,408 | A | | 12/1993 | Breyer et al. | |
| 5,406,952 | A | * | 4/1995 | Barnes et al. | 600/485 |
| 5,515,865 | A | * | 5/1996 | Scanlon | 600/534 |
| 6,368,275 | B1 | * | 4/2002 | Sliwa et al. | 600/437 |

FOREIGN PATENT DOCUMENTS

| EP | 0 506 030 | 9/1992 |
| WO | WO 98/31279 | 7/1998 |
| WO | WO 99/53972 | 10/1999 |
| WO | WO 00/56397 | 9/2000 |

OTHER PUBLICATIONS

"Klinische Erfahrungen mit einem auf dem Rechtsventrikulären dP/dt basierenden VVIR–Schrittmachersystem," Heynen et al, Herzschrittmacher, vol. 13, No. 1 (1993) pp. 34–44, no month.

* cited by examiner

Primary Examiner—William Oen
(74) Attorney, Agent, or Firm—Schiff Hardin LLP

(57) ABSTRACT

A fluid pressure sensor for a lead or catheter intended for placement in a living organism, such as a human heart, includes a rigid annular or tubular supporting structure and a piezoelectric element disposed on at least a portion of the outer surface thereof. The piezoelectric element delivers an electrical signal when subjected to a pressure variation, and exhibits circumferential sensitivity. The rigidity of the sensor is defined to satisfy predetermined criteria to ensure that the sensor, when sensing pressure transferred to the sensor through an on-growth of tissue on the sensor, which is at least 90% of the signal which the sensor would emit without the on-growth.

14 Claims, 3 Drawing Sheets

PIEZOELECTRIC SENSOR IN A LIVING ORGANISM FOR FLUID PRESSURE MEASUREMENT

This application is a 371 of PCT/SE01/02345, filed Oct. 24, 2001.

BACKGROUND OF THE INVENTION

1. Field of the Invention

The present invention relates to a pressure sensor for mounting in the distal end portion of a lead or catheter intended to be placed in a living organism, such as the heart of a human being, of the type having a piezoelectric element delivering an electric signal when subjected to a pressure variation.

2. Description of the Prior Art

With the aid of a pressure sensor in the heart, tachycardias, such as fibrillation, can be detected and distinguished. Atrial fibrillation e.g. can be separated from ventricular fibrillation and electrical activity can be separated from mechanical activity. This is of importance for controlling the type of stimulation therapy to be delivered by a heart stimulator.

From the time derivative of the blood pressure, dP/dt, an indication is obtained of the contractility of the heart, which in turn is a measure of the degree of work of the body. In H. Heynen at al. "Klinische Erfahrungen mit einem auf dem rechtsventrikulären dP/dt basierenden VVIR-Schrittmachersystem", Herzchrittmacher, Ausgabe 13, Nr. 1, pp.34–44, 1993 rate adaptive pacing based on right ventricular $dP/dt_{max}$ is described. A general problem with this kind of measurement is to avoid flow generated pressure components, and for the kind of pressure measurement described it is desirable that the sensor is sensitive to pressure variations all around the periphery of the sensor.

U.S. Pat. No. 5,271,408 discloses a pacing lead with a flow meter for measuring intravascular blood flow having piezoelectric sensors that are sensitive to pressure variations all around the periphery of the sensor. In order to function correctly, the flow meter should be centered in the flow to be measured.

None of the devices described in the above documents relate to a device for determining capture by means of pressure and none of the above documents address the problem of overgrowth that might cover the pressure sensors and that thus might affect the measurements.

SUMMARY OF THE INVENTION

An object of the present invention therefore is to provide a pressure sensor, which is sensitive to pressure variations all around its periphery and which will not be affected by overgrowths.

This object is achieved in accordance with the invention in a fluid pressure sensor for a lead or catheter intended to be placed in a living organism, having a piezoelectric element which emits an electrical signal when subjected to a pressure variation, the piezoelectric element exhibiting circumferential sensitivity and being disposed on at least a portion of the outer surface of a rigid annular or tubular supporting structure, and wherein the rigidity of the sensor is designed to satisfy specific criteria relating to charge generated by the sensor and specific criterion related to the amplitude of the signal emitted by the sensor.

The criteria relating to the charge generation is that the charge generated by the sensor when the sensor is covered by a 1 mm thick layer of a silicon elastomer having a modulus of elasticity of at least 1.49 Mpa (as measured with 6% deformation of the material) and is immersed in distilled water at 20° C. to a depth of 50 mm in a pressure chamber and is subject to an increase of pressure amounting to 2 kPa, is at least 90% of the charge generated by the sensor when immersed into distilled water 20° C. to a depth of 50 mm in a pressure chamber and subjected to an increase of 2 kPa, but not covered with the silicon elastomer layer.

The criteria related to the signal amplitude are that the amplitude of the signal from the sensor when the sensor is covered by a 1 mm thick layer of the aforementioned commercially available silicon elastomer and is immersed in distilled water at 20° C. to a depth of 50 mm in a pressure chamber and is subjected to a pressure increase varying sinusoidally between 0 and 2 kPa at a frequency increasing from 1 to 30 Hz over the entire frequency range between 1 and 30 Hz, does not deviate more than 3 dB from the amplitude of the signal obtained from the sensor when the sensor is immersed in distilled water at 20° C. to a depth of 50 mm in a pressure chamber and is subjected to a pressure increase varying sinusoidally between 0 and 2 kPa at a frequency increasing from 1 to 30 Az, but not covered by the silicon elastomer.

The invention is based on the insight that the signal from a sensor body having a specified rigidity essentially will not be affected by overgrowth since the overgrowth simply will transmit the pressure changes in a manner similar to the way pressure is transmitted by a liquid. The reason for this is the large difference in rigidity or compliance between the sensor and the overgrowth. The overgrowth will have properties similar to the properties of ordinary cardiac tissue, i.e. have a large compliance.

The pressure sensor thus has a piezoelectric element disposed on at least parts of the outer surface of a rigid annular or tubular supporting structure. Alternatively, the piezoelectric element itself is formed as an annular or tubular rigid body.

By disposing the piezoelectric element on the outer surface of a rigid supporting structure the piezoelectric element can be made of comparatively hard material necessitating only small movements or deformations of the piezoelectric material to obtain reliable measurement signals. This results in the pressure being sensed substantially without distortion.

The sensor according to the invention can be used to detect evoked response, that is the response by the heart to stimulation pulses from a heart stimulator. After the stimulation of a heart, verification is needed that the heart actually did contract. This contraction is normally verified by study of the electrical activity of the heart, by a so-called IEGM. With a pressure sensor according to the invention this detection of the heart response to a stimulation pulse can be detected in a reliable way by measuring the blood pressure.

Further, the pressure sensor according to the invention will function correctly even if the sensor should happen to be positioned against a heart wall since the sensor is sensitive in all radial directions. By forming the supporting structure of the sensor annular or tubular the advantage is obtained that electric conductors and guide wires can easily be passed through the sensor to the electrode tip.

The supporting structure can be formed of e.g. titanium, titanium alloy, titanium nitride, platinum, platinum alloy, niobium, niobium alloy, tantalum, tantalum alloy or carbon. The layer of conductive material applied to the piezoelectric element may be formed of e.g. titanium, titanium alloy, titanium nitride, platinum, platinum alloy, carbon, niobium, niobium alloy, tantalum, tantalum alloy or gold, since these materials are biocompatible.

In an embodiment of the sensor according to the invention a low impedance charge amplifier is connected to the electrodes of the piezoelectric element to measure charge signals generated by the piezoelectric element when subjected to pressure variations. The piezoelectric element has a capacitance on the order of 1 nF and the lead has a leakage resistance that can be as low as about 50 kohm. These properties of the sensor result in the sensor forming a high-pass filter having a cut-off frequency of about 3 kHz. With the sensor according to the invention it is desirable to measure frequencies down to e.g. 0.2 Hz. With the above-mentioned embodiment of the sensor according to the invention this problem is solved by short-circuiting the piezoelectric element and measuring the charge generated in the piezoelectric material instead of measuring the voltage from the piezoelectric element. Expressed in other words, the signal from the piezoelectric element is consequently amplified by a charge amplifier with low input impedance instead of by a voltage amplifier in order to avoid the necessity of a high insulation resistance between the conductors of the piezoelectric element.

DESCRIPTION OF THE PREFERRED EMBODIMENTS

Figure 1:
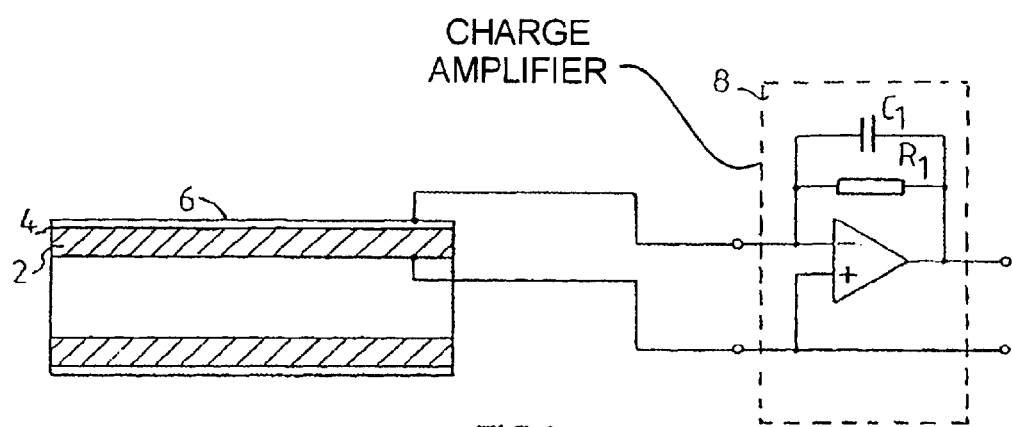
FIGS. 1 through 3 show three embodiments of the sensor according to the invention in longitudinal section, connected to a charge amplifier in FIGS. 1 and 2.

In FIG. 1 shows a longitudinal section of a first embodiment of the sensor according to the invention. This embodiment has a sensing element in the form of a tube 2 which on its outer surface is covered with a layer 4 of a piezoelectric material, preferably a ceramic piezoelectric material. Preferred materials are PZT and potassium-sodium-niobate. The layer may be applied on the tube 2 by sputtering, laser-ablation or any other suitable method. On the outer surface of the piezoelectric layer 4 a layer 6 of a conductive material, e.g. titanium, titanium alloy, titanium nitride, platinum, platinum alloy, carbon, niobium, niobium alloy, tantalum or tantalum alloy is applied in a similar way. In this way the tube 2 and the layer 6 form electrodes which are connected to an amplifier 8 for measuring the charge produced in the piezoelectric layer 4 when it is subject to pressure variations.

Figure 5:
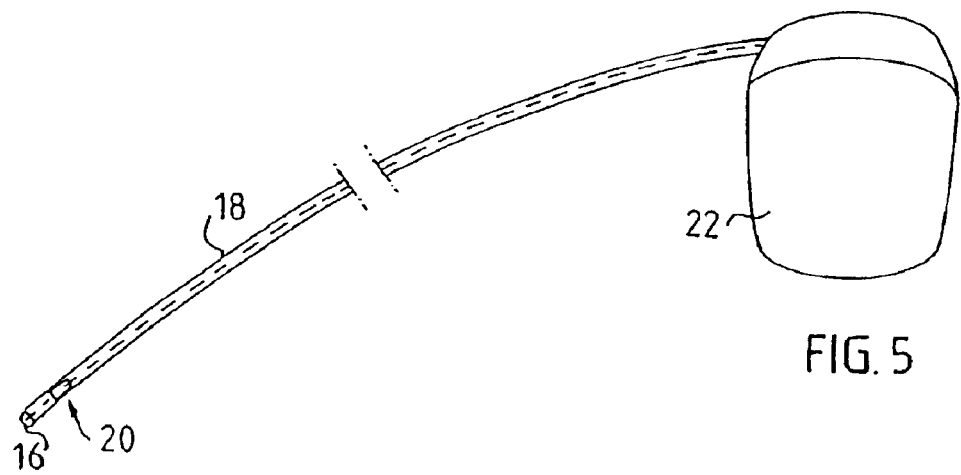
FIG. 5 illustrates the mounting of a sensor according to the invention in a pacing lead.

The tube 2 is a rigid tube, that may be placed inside the outer silicon rubber insulation of a pacing lead 18 with the electrodes connected through two conductors to a charge amplifier mounted in the pacemaker, see FIG. 5. Alternatively, human tissue can replace one of the conductors, i.e. the piezoelectric material is in direct contact with blood or tissue. In this case the piezoelectric material should have such properties that the material is considered biocompatible.

In the case of a bipolar lead the sensor can be positioned outside the inner coiled conductor and the inner silicon insulation but inside the outer silicon insulation.

Suitable materials for the tube 2 and the conducting layer 6 are for instance titanium, titanium alloy, titanium nitride, platinum, platinum alloy, niobium, niobium alloy, tantalum, tantalum alloy or carbon and titanium, titanium alloy, titanium nitride, platinum, platinum alloy, carbon, niobium, niobium alloy, tantalum, tantalum alloy or gold.

Figure 2:
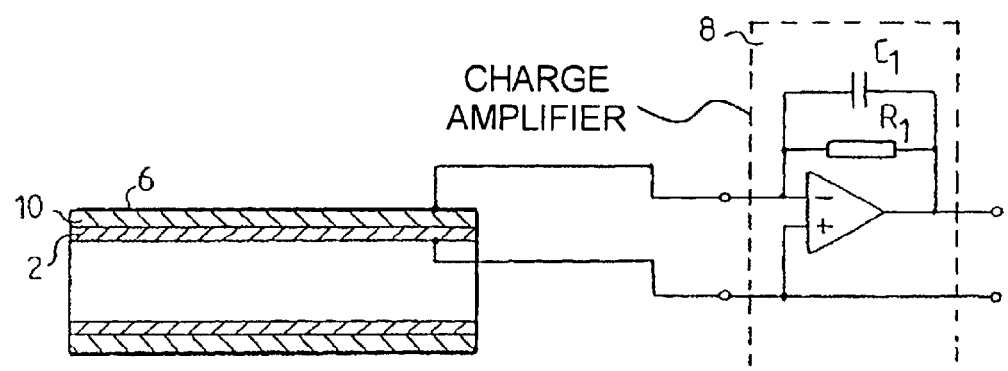

FIG. 2 shows a second embodiment of the sensor according to the invention having a tube of a piezoelectric material 10 disposed around the inner tube 2 of platinum—iridium alloy, titanium or carbon. Electric contact between these two tubes 2, 10 may be formed for example, with an electrically conducting glue. On the outer surface of the piezoelectric tube 10 a conducting layer 6 is applied as in the embodiment in FIG. 1. Also, like in the previously described embodiment, the tube 2 and the layer 6 form electrodes that are connected to a charge amplifier 8 mounted in a pacemaker for measuring electrical charges generated in the piezoelectric tube, when the tube is subjected to radial pressure variations.

Figure 3:
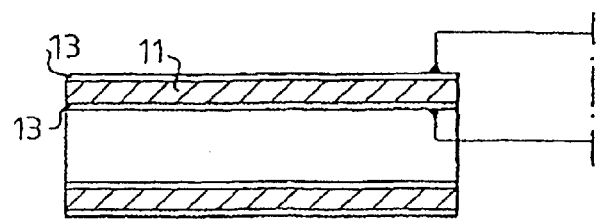

FIG. 3 shows a third embodiment of the sensor element of the sensor according to the invention having a rigid tube 11 of a piezoelectric material with inner and outer electrodes 13, i.e. the supporting structure and the piezoelectric layer are both made of piezo-electric material and may also be made of the same material. In this case the tube is provided with an inner conducting layer as well.

Figure 4:
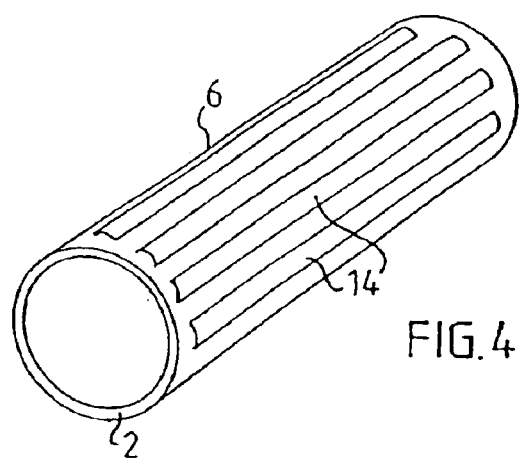
FIG. 4 shows an alternative embodiment of the sensor configuration.

FIG. 4 shows an embodiment in which the piezoelectric element is formed as longitudinal strips 14 of piezoelectric material distributed around the outer surface of the supporting tube 2 with gaps or spaces respectively between the strips 14.

As mentioned above an important feature of the sensor according to the invention resides in the fact that it is sensitive to pressure variations all around its periphery. Thus it will operate reliable also if it should happen to be positioned against a heart wall. Since the sensor has an annular or tubular design electric conductors and guide wires can easily be passed through the sensor to the electrode tip 16. This can for instance be seen in FIG. 5 illustrating the positioning of a pressure sensor according to the invention in a lead 18 at 20 in the distal end portion.

Since the pressure sensor according to the invention has a rigid supporting structure for the piezoelectric element, this element can be chosen such that only small deformations are needed to get reliable measurement signals. The operation of the sensor thus will not be affected by overgrowths.

The rigidity of the sensor depends on the material in the support and/or the piezoelectric material, on the amount of material and on the shape of the sensor and the rigidity required by the invention thus can be obtained in a number of ways.

The rigidity of the sensor thus preferably is defined with the aid of a silicon elastomer having a modulus of elasticity of at least 1.49 MPa measured at a deformation of 6%. One example of a suitable commercially available elastomer is "Sylgard® 567 Primerless Silicone Encapsulant" manufactured by DOW CORNING CORPORATION, Midland, Mich. (this standard silicon elastomer further has a durometer hardness of 38 points Shore A according to CTM 0099, a tensile strength of 200 psi(1,38 MPa) according to CTM 0137A, an elongation of 100% according to CTM 0137A, a specific gravity of $1.24 \times 10^3$ kg/in$^3$ at 25° C. according to CTM 0022, a volume coefficient of thermal expansion of $8.49 \times 10^{-4}$ CC/CC° C. according to CTM 0653 and a lap shear of 200 psi (1,38 MPa) according to CTM 0243, all based on a sample thickness of 125 mils (3.2 mm)). For omparison it should however be noted that a solid sensor element made of potassium-sodium-niobate (which is the preferred material) would have a modulus of elasticity of about 80 GPa.

When the rigidity of the sensor is to be determined, the sensor is first immersed in distilled water at 20° C. to a depth of 50 mm in a pressure chamber and the pressure is increased with 2 kPa. The charge generated in the sensor by the increase of pressure is then measured by means of an electrometer. The sensor is removed from the pressure chamber and dried. The active parts of the sensor are then covered with a 1 mm thick layer of the silicon elastomer defined above and the sensor is again immersed in distilled water in the pressure chamber to a depth of 50 mm. The pressure in the pressure chamber is again raised to 2 kPa and the charge generated in the sensor is again measured by means of an electrometer. If the charge is 90% of the previous signal or more, then a first requirement for the rigidity of the sensor has been met.

The above test is then repeated with the difference that the pressure is varied sinusoidally up to 2 kPa, starting with a frequency of 1 Hz. The frequency is increased from 1 to 30 Hz and the amplitude of the signal from the sensor is measured. The amplitude of the signal from the sensor, when covered by said layer of silicon elastomer, should not deviate more than 3 dB from the amplitude of the signal from a sensor not covered with silicon elastomer over the entire frequency range between 1 and 30 Hz. This is the second requirement for the rigidity of the sensor. The pressure for instance could be varied by means of pulsed pressurized air or by means of a movable plunger forming one wall, or a part thereof, of the pressure chamber.

Figure 6:
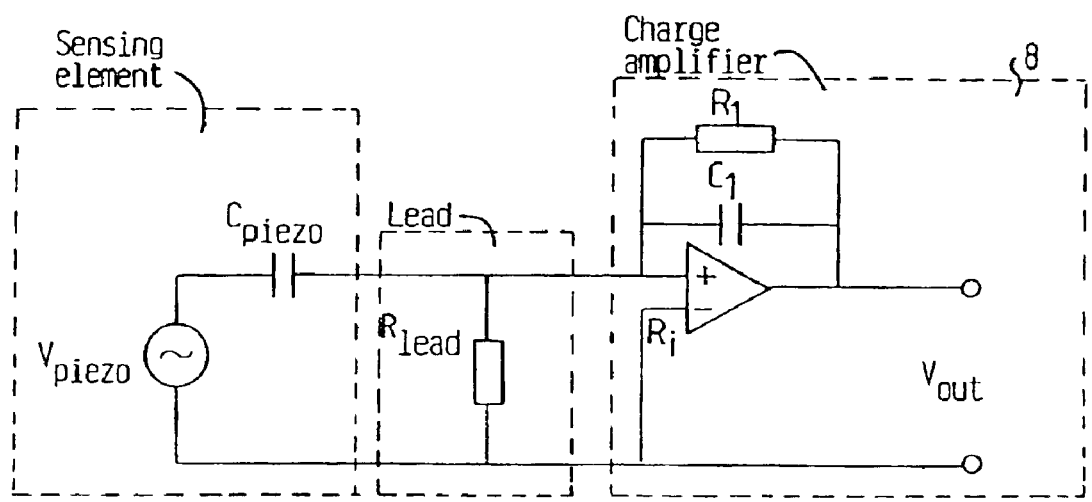
FIG. 6 shows the equivalent electrical circuit of the sensor in FIGS. 1 and 2 connected to a charge amplifier.

The piezoelectric element can electrically be represented as a voltage source V in series with a capacitance $C_{piezo}$. The lead can electrically be represented as a resistance $R_{lead}$, see FIG. 6. The piezoelectric element forming the sensing element is connected through the lead to a charge amplifier, located inside the pacemaker 22. The capacitance $C_{piezo}$ of the piezo-element is normally on the order of 1 nF and the insulation resistance $R_{lead}$ between the lead wires can be as low as 50 kohm. These two quantities form a high-pass filter having a cut-off frequency of the order of kHz, in the worst situation of approximately 3 kHz, when a voltage amplifier is used. With the sensor according to the invention it is desirable to measure pressure variations of frequencies down to 0.2 Hz. This problem is solved in the sensor according to the invention by connecting to the piezoelectric element a charge amplifier 8 having a low input resistance $R_i$ for measuring the charge produced in the piezoelectric element, when it is subjected to pressure variations, instead of measuring the voltage from the piezoelectric element. The amplification in this case is given by the ratio $C_{piezo}/C_1$ and the cut-off frequency is equal to $1/(2\pi R_1 C_1)$. As can be seen from FIG. 5 the piezoelectric element in practice will be short-circuited by the input resistance $R_i$ of the charge amplifier 8 and the requirement for a high insulation resistance between the conductors of the piezoelectric element is eliminated.

If the sensor is to be covered with a layer of silicone, polyurethane or similar in use, then the test silicon layer is applied on top of this layer.

The above definitions of the rigidity is based on the rationale that the compliance of the silicon elastomer is close to but less than the compliance of tissue grown on the sensor and thus can be used to define the rigidity of the sensor.

Although normally a rigidity resulting in a charge from a covered sensor that is 90% of the charge from the not covered the sensor normally is sufficient, of course it would be preferable if the rigidity is such that charges amounting to more that 95% were obtained, for instance 97%, 99% or even approaching 100%.

The silicon elastomer in the embodiment illustrated above preferably is in the form of a commercially available silicon tube having suitable dimensions. A length of the tube is simply pulled over the sensor, care being taken that the tube extends well past the ends of the sensor. The layer of silicon elastomer however also could be applied by dipping the sensor in liquid, uncured silicon elastomer, if necessary several times until the required thickness has been obtained, and then curing the elastomer.

Although modifications and changes may be suggested by those skilled in the art, it is the invention of the inventor to embody within the patent warranted heron all changes and modifications as reasonably and properly come within the scope of his contribution to the art.

What is claimed is:

1. A fluid pressure sensor for a lead or catheter adapted to be placed in a living organism, said sensor comprising a rigid, annular supporting structure and a piezoelectric element delivering an electric signal when subjected to a pressure variation, said piezoelectric element exhibiting circumferential sensitivity and being disposed on at least a portion of an outer surface of said rigid annular supporting structure, said sensor having a rigidity such that a) the charge generated by said sensor when said sensor is covered by a 1 mm thick layer of a silicon elastomer having a modulus of elasticity of at least 1.49 MPa (as measured with 6% deformation of the material) and is immersed in distilled water at 20° C. to a depth of 50 mm in a pressure chamber and is subjected to an increase of pressure amounting to 2 kPa, is at least 90% of the charge generated by said sensor when immersed into distilled water at 20° C. to a depth of 50 mm in a pressure chamber and subjected to an increase of pressure of 2 kPa but not covered with said silicon elastomer layer, and b) the amplitude of the signal from said sensor when said sensor is covered by a 1 mm thick layer of said silicon elastomer and is immersed in distilled water at 20° C. to a depth of 50 mm in a pressure chamber and is subjected to a pressure increase varying sinusoidally between 0 and 2 kPa at a frequency increasing from 1 to 30 Hz over an entire frequency range between 1 and 30 Hz does not deviate more than 3 dB from the amplitude of the signal obtained from said sensor when said sensor is immersed in distilled water at 20° C. to a depth of 50 mm in a pressure chamber and subjected to a pressure increase varying sinusoidally between 0 and 2 kPa at a frequency increasing from 1 to 30 Hz but not covered by said silicon elastomer.

2. The sensor according to claim 1, wherein the piezoelectric element comprises a layer of piezoelectric material on the outer surface of said supporting structure.

3. The sensor according to claim 1, wherein the piezoelectric element comprises a plurality of strips of piezoelectric material distributed with interspaces therebetween around the outer surface of the supporting structure.

4. The sensor according to claim 1, wherein the piezoelectric element comprises a tube of piezoelectric material disposed around said rigid supporting structure.

5. The sensor according to claim 1 wherein said supporting structure is comprised of a piezoelectric material.

6. The sensor according to claim 5, wherein said supporting structure is comprised of a piezoelectric material different from the material comprising the piezoelectric layer.

7. The sensor according to claim 1 wherein said supporting structure is formed of material selected from the group consisting of titanium, titanium alloy, titanium nitride, platinum, platinum alloy, niobium, niobium alloy, tantalum, tantalum alloy and carbon.

8. The sensor according to claim 1 wherein said supporting structure comprises a rigid tube.

9. The sensor according to claim 1 wherein conductive material disposed in contact with the piezoelectric element to form an electrode, said layer being formed of a material selected from the group consisting of titanium, titanium alloy, titanium nitride, platinum, platinum alloy, carbon, niobium, niobium alloy, tantalum and tantalum alloy.

10. The sensor according to claim 8, comprising a low input impedance charge amplifier connected to the electrode of the piezoelectric element to measure charge signals generated by the piezoelectric element when subjected to pressure variations.

11. The sensor according to claim 1 wherein the piezoelectric element comprises a ring of piezoelectric material disposed around said rigid supporting structure.

12. The sensor according to claim 1 wherein said supporting structure comprises a rigid ring.

13. A medical lead adapted for placement in a living organism, comprising a rigid, annular supporting structure carried by said lead body, and a piezoelectric element delivering an electric signal when subjected to a pressure variation, said piezoelectric element exhibiting circumferential sensitivity and being disposed on at least a portion of an outer surface of said rigid annular supporting structure, said sensor having a rigidity such that a) the charge generated by said sensor when said sensor is covered by a 1 mm thick layer of a silicon elastomer having a modulus of elasticity of at least 1.49 MPa (as measured with 6% deformation of the material) and is immersed in distilled water at 20° C. to a depth of 50 mm in a pressure chamber and is subjected to an increase of pressure amounting to 2 kPa, is at least 90% of the charge generated by said sensor when immersed into distilled water at 20° C. to a depth of 50 mm in a pressure chamber and subjected to an increase of pressure of 2 kPa but not covered with said silicon elastomer layer, and b) the amplitude of the signal from said sensor when said sensor is covered by a 1 mm thick layer of said silicon elastomer and is immersed in distilled water at 20° C. to a depth of 50 mm in a pressure chamber and is subjected to a pressure increase varying sinusoidally between 0 and 2 kPa at a frequency increasing from 1 to 30 Hz over an entire frequency range between 1 and 30 Hz does not deviate more than 3 dB from the amplitude of the signal obtained from said sensor when said sensor is immersed in distilled water at 20° C. to a depth of 50 mm in a pressure chamber and subjected to a pressure increase varying sinusoidally between 0 and 2 kPa at a frequency increasing from 1 to 30 Hz but not covered by said silicon elastomer.

14. A medical lead as claimed in claim 13 wherein said lead body is a bipolar lead body having an inner insulating layer and an outer insulating layer and a lead body axis, and wherein said sensor is mounted coaxially with said lead body axis between said inner insulating layer and said outer insulating layer.

* * * * *